United States Patent
Keyes et al.

[11] Patent Number: 6,084,079
[45] Date of Patent: Jul. 4, 2000

[54] PROCESS FOR PREPARING N-DEMETHYL-N-ALKYL ERYTHROMYCIN DERIVATIVES

[76] Inventors: Robert F. Keyes, 3621 109th St., Kenosha, Wis. 53142; Hemant H. Patel, 1552 Acorn Ct.; Ramiya H. Premchandran, 6658 Foxworth La., both of Gurnee, Ill. 60031; Albert V. Thomas, 1525 Eric La., Libertyville, Ill. 60048; Anne H. Kemp, 1365 Michele Dr., Palatine, Ill. 60067

[21] Appl. No.: 09/080,340

[22] Filed: May 15, 1998

[51] Int. Cl.7 .............................. C07H 1/00; C07H 17/08
[52] U.S. Cl. ............................................. 536/7.2; 536/18.5
[58] Field of Search ..................... 536/7.2, 18.5

[56] References Cited

U.S. PATENT DOCUMENTS

| | | | |
|---|---|---|---|
| 3,725,385 | 4/1973 | Freiberg | 536/7.2 |
| 5,578,579 | 11/1996 | Lartey et al. | 579/25 |
| 5,760,198 | 6/1998 | Parekh et al. | 536/7.2 |

FOREIGN PATENT DOCUMENTS

WO9313780  7/1993  WIPO .

OTHER PUBLICATIONS

P.A. Lartey, et al., J. Med. Chem., 38 (1793–1798 1995); "Synthesis of 4"—\ Deoxy Motilides: Identification of a Potent and Orally Active Prokinetic Drug Candidate.

*Primary Examiner*—Elli Peselev
*Attorney, Agent, or Firm*—Portia Chen; Mona Anand

[57] ABSTRACT

The claimed invention relates to a novel process of preparing N-demethyl-N-alkyl-4"-deoxy erythromycin A and B. The process comprises protecting the 2'-hydroxy or the 2'- and 11-hydroxy of a N-demethyl-4"-deoxy erythromycin derivative having the formula:

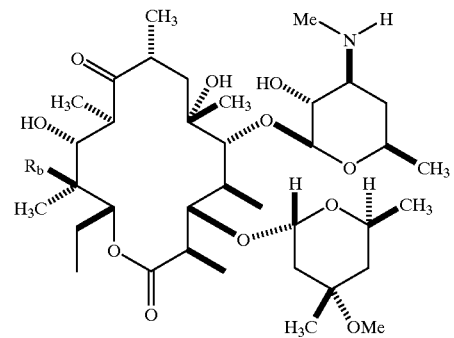

where $R_b$ is H or OH, with a silyl protecting group and alkylating the N-position of the desosamine sugar.

17 Claims, No Drawings

PROCESS FOR PREPARING N-DEMETHYL-N-ALKYL ERYTHROMYCIN DERIVATIVES

TECHNICAL FIELD

The present invention relates to a novel process for the preparation of N-demethyl-N-alkyl-erythromycin derivatives via 2'-silylated erythromycin derivatives. The N-demethyl-N-alkyl-erythromycin derivatives are useful in the preparation of 8,9-didehydro-N-demethyl-6,9-epoxy-N-alkylerythromycin derivatives having prokinetic activity.

BACKGROUND OF THE INVENTION

Erythromycins A through D, represented by formula (E),

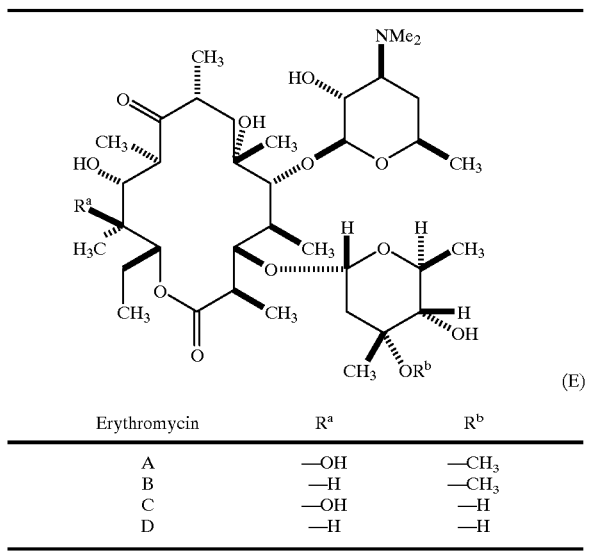

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection.

Some erythromycin derivatives have use as prokinetic agents. For example, an erythromycin B derivative, having formula I below:

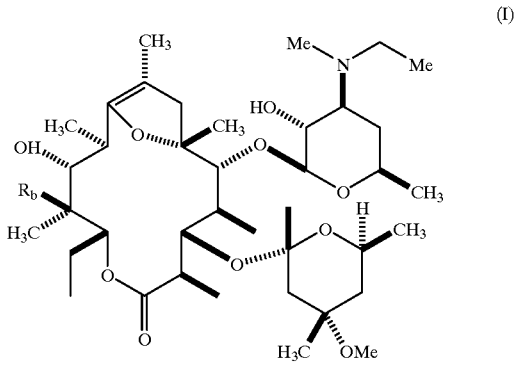

has been described as a prokinetic agent having use in the treatment of gastrointestinal motility disorders (see P. A. Lartey et al., *J. Med Chem.*, 38 (1793–1798 (1995); and R. Faghih, et al., PCT application WO 9313780, published Jul. 22, 1993). U.S. Pat. No. 5,578,579 describes 4"-deoxyerythromycin derivatives having prokinetic activity.

The first step of the process for preparing these prokinetic compounds requires the N-demethylation step to obtain a compound having the formula:

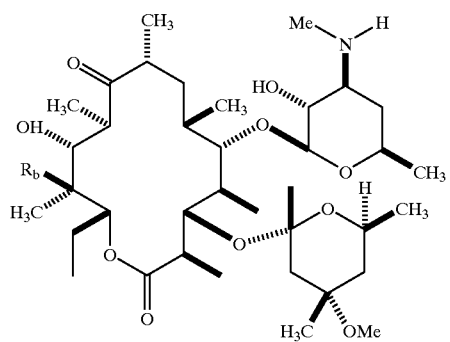

wherein $R_b$ is H or OH. The N-demethyl-erythromycin derivatives having the above formula are obtained by the process described in issued U.S. application Ser. No. 08/754, 867. The process disclosed therein involves preparation of 3'-N-demethyl-erythromycin derivatives by step-wise addition of iodine in a pH-adjusted solution from 40° C. to 70° C. U.S. Pat. No. 5,578,579 describes a process of making N-demethyl-N-alkyl erythromycin derivatives wherein a 3'-N-dimethyl hemiketal derivative is first treated with iodine in the presence of a suitable base, such as sodium acetate, and then reacted with an alkyl halide and a hindered base. Alternatively, U.S. Pat. No. 3,725,385, issued Apr. 3, 1973, describes a process in which erythromycin derivatives are demethylated by a one-step treatment with a single addition of iodine in a pH-adjusted solution from −10° C. to 50° C.

Previous methods of N-alkylating the N-demethyl-erythromycin derivatives to obtain the prokinetic compound of formula (I) often result in formation of a quaternary salt which prevents completion of the reaction process and reduces yield of the N-demethyl-N-alkyl product.

Therefore, there continues to be a need to provide a rapid, efficient method of preparing the N-demethyl-N-alkyl erythromycin derivatives to ensure more efficient synthesis and wider availability of the desired prokinetic agents.

SUMMARY OF THE INVENTION

The present invention relates to a process of preparing N-demethyl-N-alkyl-erythromycin derivatives having the formula:

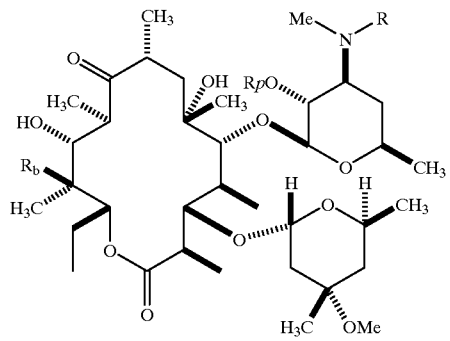

wherein R is a loweralkyl group, $R_b$ is H or OH, and $R_p$ is hydrogen or a silyl protecting group, comprising:

a.) protecting a N-demethyl erythromycin A or B compound having the formula:

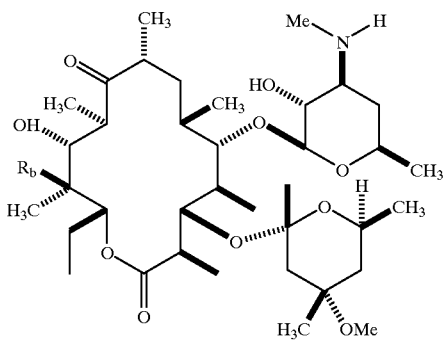

wherein $R_b$ is H or OH, with a silyl protecting group to form a protected-N-demethyl-erythromycin derivative; and b.) alkylating the protected-N-demethyl-erythromycin derivative.

The N-demethyl-N-alkyl-erythromycin derivatives can be enolized to form a 8,9-didehydro-N-demethyl-6,9-epoxy-N-alkylerythromycin derivative having prokinetic activity.

The process of the present invention provides efficient and improved methods for preparing N-demethyl-N-alkyl-erythromycin A or B compounds, which are useful as prokinetic agents in treating gastrointestinal motility disorders.

DETAILED DESCRIPTION OF THE INVENTION

The present invention relates to a process of preparing N-demethyl-N-alkyl-erythromycin A and B derivatives. In particular, the invention relates to protecting the 2'- and optionally 11-hydroxy groups with silyl protecting groups to form a N-demethyl-N-alkyl erythromycin A or B compound. The protected erythromycin derivative is reacted with an alkylating reagent in the presence of a base to alkylate the N-demethyl-erythromycin starting material. Enolization affords a 8,9-didehydro-N-demethyl-6,9-epoxy-N-alkylerythromycin derivative.

A number of defined terms are used herein to designate particular elements of the present invention. When so used, the following meanings are intended:

The term "alkylating reagent" as used herein refers to a substituent capable of placing an $C_1$–$C_4$ group onto a nucleophilic site, including, but not limited to, alkyl halides, for example ethyl chloride, ethyl iodide, and ethyl bromide, and diethyl sulfate.

The term "loweralkyl" or "alkyl" as used herein refers to straight or branched chain alkyl radicals containing from 1 to 4 carbon atoms including, but not limited to, methyl, ethyl, n-propyl, isopropyl, n-butyl, isobutyl, sec-butyl, t-butyl, and the like.

The term "silyl" refers to a group of the formula Si $(R_1)(R_2)(R_3)$ where each of $R_1$, $R_2$, and $R_3$ are independently hydrogen, lower alkyl, aryl, phenyl, phenyl-substituted lower alkyl, cycloalkyl or alkenyl; $(R_1R_2R_3Si)_nO$ where $R_1$, $R_2$, and $R_3$ are independently selected from the group comprising hydrogen and methyl; and $R_3Si$—X where X is a halide including chlorine, bromine, and iodine, or p-toluenesulfonate.

The term "silyl protecting group" or "hydroxy-protecting group" as used herein refers to a substituent which protects hydroxyl functionalities against undesirable reactions during synthetic procedures such as those groups disclosed in Greene, "Protective Groups in Organic Synthesis," (John Wiley & Sons, New York (1981)), which is incorporated herein by reference. Silyl protecting groups comprise alkyl silanes, for example, trimethylsilane, t-butyldimethylsilane, and t-butyldiphenylsilane; silicon halides, for example, trimethylsilyl chloride, diphenylmethylsilyl chloride, and diethylmethylsilyl chloride; and silyl ethers, for example, trimethylsilyl ether, t-butyldimethylsilyl ether, and t-butyldiphenylsilyl ether.

The term "silylating reagent" or "hydroxy-protecting reagent" as used herein refers to those reagents which react with the hydroxy functionality to give the hydroxy protected groups described above. For example, the hydroxy-protecting reagent trimethylsilane affords the trimethylsilyl hydroxy-protecting group. These reagents are described in Greene, "Protective Groups In Organic Synthesis," (John Wiley & Sons, New York (1981)).

Abbreviations which have been used in the descriptions of the scheme and the examples that follow are: DMF for dimethylformamide; DMSO for dimethyl sulfoxide; THF for tetrahydrofuran; TLC for thin layer chromatography; HMDS for hexamethyldisilazane; and NMP for N-methylpyrrolidone.

The silylation and alkylation reactions of the invention can be accomplished in one-pot or in a step-wise manner. The step-wise process of the invention relates to a process of protecting a N-demethyl-erythromycin starting material via silylation and isolating the protected product for use in a subsequent alkylation step. A one-pot process in accordance with the invention relates to silylating a N-demethyl-erythromycin starting material and charging the reaction mixture with an alkylating reagent and a base. Isolation of a protected N-demethyl-erythromycin derivative is not accomplished. The prepared N-demethyl-N-alkyl-erythromycin derivatives can be enolized to form 8,9-didehydro-N-demethyl-6,9-epoxy-N-alkylerythromycin derivatives having prokinetic activity.

In a process of the invention as illustrated in Scheme 1, a protected-N-demethyl-erythromycin intermediate of the silylation step is isolated and subsequently treated with an alkylating reagent in an alkylation step. A N-demethyl-erythromycin starting material having a formula:

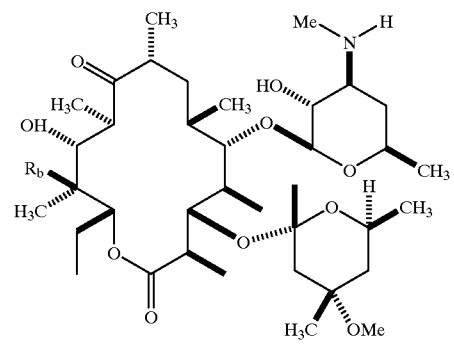

wherein $R_b$ is H or OH, is treated with a silylating reagent at room temperature to protect the 2'- and optionally the 11-positions of the N-demethyl-erythromycin. Treating the silylated N-demethyl-erythromycin compound with an alkylating reagent in the presence of a base affords a N-demethyl-N-alkyl-erythromycin derivative.

Scheme 1

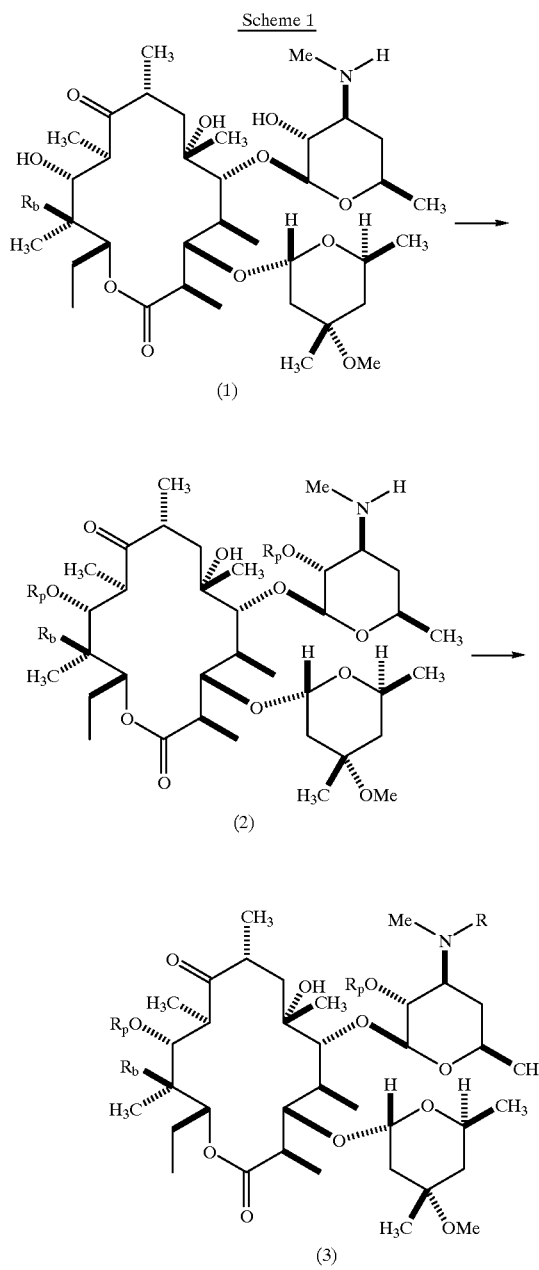

In accordance with Scheme 1, Compound (1), wherein $R_b$ is hydrogen or hydroxy, is protected with a silyl protecting group to form Compound (2), wherein $R_p$ is independently hydrogen or a silyl protecting group at each occurrence. Protection of the 2'- and optionally the 11-hydroxy groups is accomplished by reacting the N-demethyl-4"-deoxy erythromycin starting material with a silyl protecting reagent in a suitable solvent. The reaction is generally carried out at room temperature for about 8 to 10 hours or until completion of the silylation reaction. The preferred method of monitoring the reaction is thin layer chromatography using a solvent mixture of approximately 80 $CHCl_3$/17 MeOH/23 toluene performed with p-anisaldehyde stain.

Exemplary and preferred silyl protecting reagent have the formula:

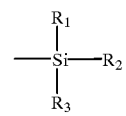

wherein $R_1$, $R_2$, and $R_3$ are each independently selected from the group consisting of triisopropyl, t-butyldimethyl, triethyl, isopropyldimethyl, t-butyldiphenyl, methyldiisopropyl, methyldi-t-butyl, tribenzyl, and triphenyl; $(R_1R_2R_3Si)_nO$ where $R_1$, $R_2$, and $R_3$ are each independently selected from the group consisting of hydrogen and methyl; and $R_3Si$—X, where X is a halide including chlorine, bromine, and iodine, or p-toluensulfonate. Examples of reagents suitable for protecting 2'- and optionally the 11-hydroxy groups include, but are not limited to: trimethylsilyl chloride; hexamethyldisiloxane/ethylamino-p-toluenesulfonate; N,O-bis(trimethylsilyl)acetamide/DMF; ethyl(trimethylsilyl)acetate/n-butylammonium fluoride; trimethylsilyl-N-trimethysilyl carbamate; and trimethylsilyl-N-trimethylsilyl sulfamide. Preferably, $R_1$, $R_2$, and $R_3$ of the silyl protecting reagent are all methyl.

The preferred silylating reagent is hexamethyldisilazane. Where the silylating reagent is other than hexamethyldisilazane, the silylation reaction is accomplished in the presence of an organic base. Typically, approximately 2.5 equivalents of silylating reagent are reacted with one equivalent of starting material.

Suitable bases for the silylation reaction include N,N-diisopropylamine, triethylamine, pyridine, imidazole, ditrimethylsilyl amine, and dimethylaminopyridine. The preferred base is N,N-diisopropylamine. Typically, one equivalent of base is reacted with the starting material for one equivalent of silylating reagent used.

Exemplary preferred solvents include THF, dichloromethane, ethyl acetate, toluene, and acetonitrile. The preferred solvent is N-methylpyrrolidone.

Alternatively, the N-demethyl-4"-deoxy erythromycin, Compound (1), is selectively monosilylated to protect only the 2'-hydroxyl group. In this case, the reaction is sparged with an inert gas while the silylation step is carried out. Presence of the inert gas causes the monosilylated product to fall out of solution. Suitable gases include nitrogen, helium, and argon, and nitrogen is the most preferred gas.

The protected compound, Compound (2), is treated with an alkylating agent to form Compound (3), wherein R is a loweralkyl group and $R_p$ is independently selected from hydrogen or a silyl protecting group at each occurrence. The protected-N-demethyl-erythromycin derivative intermediate of the silylation step is reacted with an alkylating reagent in the presence of a base. The reaction is generally carried out between 40° C. and 45° C. in a suitable solvent.

Suitable alkylating agents comprise a compound selected from the group having the formula: R-X, wherein X is a halide, including chlorine, bromine, fluorine, iodine, sulfate, sulfonate, or p-toluensulfonate, and R is a loweralkyl group, and diethyl sulfate. Ethyl iodide is the preferred reagent. The amount of alkylating reagent used is about 2.5 equivalents for one equivalent of starting material.

Either an organic or an inorganic base is suitable for the reaction. The reaction can be carried out using triethylamine, sodium dichloroacetate, anhydrous sodium acetate, sodium trichloroacetate, tris(trimethylsilyl)amine, and the like. Sodium bicarbonate is the preferred base. Alkylation using N,N-diisopropylethylamine (Hunig's base) as the base affords the N-demethyl-N-alkyl compound without affecting the reaction profile of the preferred reaction. Typically, from about 2.5 equivalents to 4.0 equivalents of base are used for one equivalent of starting material. When the amount of base is determined relative to the alkylating reagent, the ratio of base to alkylating reagent is from about 1:1 to about 1:1.5.

Exemplary and preferred solvents for the alkylation include THF, dichloromethane, ethyl acetate, toluene, and acetonitrile. N-methylpyrrolidone is the preferred solvent for the alkylation.

The one-pot process of preparing N-demethyl-N-alkyl-erythromycin derivatives is illustrated in Scheme 2. In this process, alkylation is accomplished without isolating the protected-N-demethyl-erythromycin intermediate. In Step (i), the N-demethyl compound is treated with a silylating reagent to protect the 2'- and optional 11-hydroxyl groups. Without isolating the protected N-demethyl-erythromycin derivative, the reaction mixture is charged in Step (ii) with an alkylating reagent and a base to afford a N-demethyl-N-alkylated erythromycin derivative.

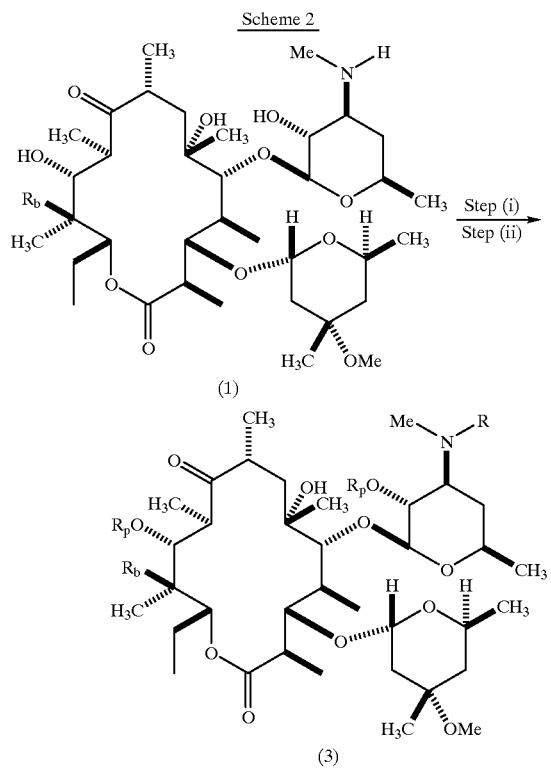

The one-pot process of the invention provides an advantage of eliminating efforts spent in isolating the protected N-demethyl-erythromycin derivative between the silylation and the alkylation reactions. The silylation and alkylation, respectively Step (i) and Step (ii), are accomplished in accordance with the process described in Scheme 1.

N-demethyl-N-alkyl-erythromycin derivative prepared according to processes of the invention can be enolized to form 8,9-didehydro-N-demethyl-6,9-epoxy-N-alkyl-erythromycin derivatives having prokinetic activity as described in PCT application WO 9313780 and U.S. Pat. No. 5,578,579. Preparation of 8,9-didehydro-N-demethyl-6, 9-epoxy-N-alkyl-erythromycin derivative is described in Scheme 3.

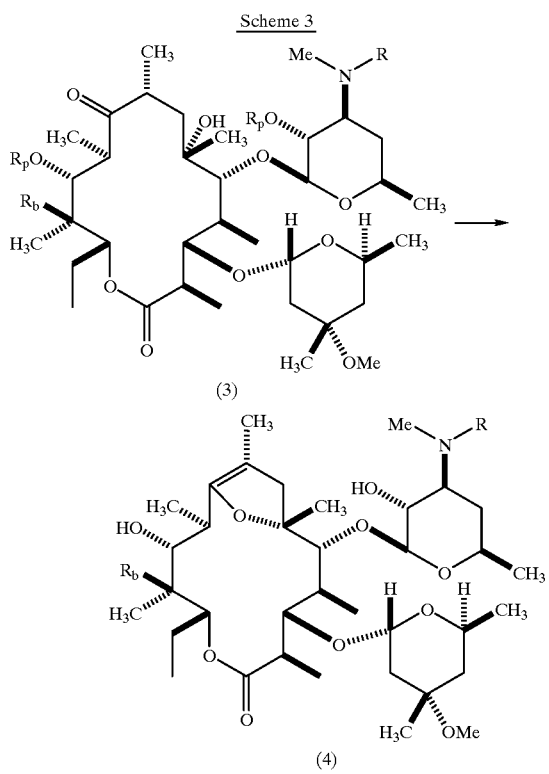

Treating a N-demethyl-N-alkyl-erythromycin derivative, Compound (3), with a weak acid enolizes the 8,9-positions to afford a 8,9-didehydro-N-demethyl-6,9-epoxy-N-alkylerythromycin derivative, Compound (4). Enolization also accomplishes deprotecting the 2'- and 11-hydroxy groups, if protected. The temperature of the reaction is maintained below 35° C. during the exothermic addition of the weak acid. However, it is preferred that the reaction is carried out between 22° C. and 35° C. The acid is preferably added over a 30 to 40 minute period. Suitable acids include trifluoroacetic acid, dichloroacetic acid, and acetic acid. The preferred weak acid is trifluoroacetic acid. Generally, the N-demethyl-N-alkyl-erythromycin derivative is treated with 2 to 10 equivalents of weak acid relative to one equivalent of the N-demethyl-N-alkyl-erythromycin compound.

In another aspect, the present invention provides certain compounds formed during a process of this invention. Such compounds correspond to the structure below:

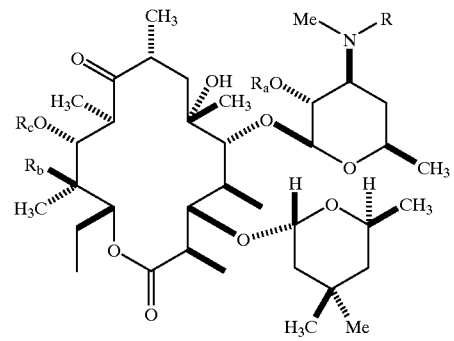

wherein R is a loweralkyl group; $R_b$ is H or OH; and $R_a$ and $R_c$ are independently selected at each occurrence from the group comprising hydrogen and a silyl protecting group having the formula:

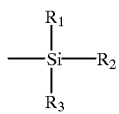

where $R_1$, $R_2$, and $R_3$ are each independently selected from the group comprising triisopropyl, t-butyldimethyl, triethyl, isopropyldimethyl, t-butyldiphenyl, methyldiisopropyl, methyldi-t-butyl, tribenzyl, and triphenyl; $(R_1R_2R_3Si)_nO$ where $R_1$, $R_2$, and $R_3$ are each independently selected from the group comprising hydrogen and methyl; and $R_3Si-X$, where X is a halide, including chlorine, bromine, and iodine, p-toluenesulfonate, or sulfonate.

A detailed description of the synthesis of N-demethyl-N-alkyl erythromycin A and B, using a process of the present invention is set forth hereinafter in the Examples.

The following Examples illustrate the preferred embodiment of the present invention. The Examples are merely illustrative and are not meant to limit the specification and claims in any way.

EXAMPLES

The N-demethyl-4"-deoxyerythromycin B used in synthesis of 2'11-bis(trimethylsilyl)-N-demethyl-4"-deoxyerythromycin B were prepared in accordance with the process as described in Example 2 of allowed U.S. application Ser. No. 08/754,867. Alternatively, the N-demethyl-4"-deoxyerythromycin B can be prepared according to the demethylation methods described in Example 1 of U.S. Pat. No. 3,725,385, issued Apr. 3, 1973.

Example 1

Silylation/Alkylation

Example 1a: Synthesis of 2',11-bis(trimethylsilyl)-N-demethyl-4"-deoxy-N-ethylerythromycin B (2a)

N-demethyl-4"-deoxyerythromycin B (50 gms, 72.6 mmol) was dissolved in N-methylprrolidinone (125 mL) and hexamethyldisilazane (38.3 ml, 181.5 mmol) was charged and stirred for 8 hours until the reaction was complete. TLC was performed (80 $CHCl_3$/17 MeOH/23 toluene) with p-anisaldehyde stain. Heptane (50 mL) was added to the reaction mixture and then distilled to remove heptane (ammonia gas being liberated). After the distillation was complete, the reaction mixture was cooled and the following reagents were charged: N,N-diisopropylethylamine (28.1 gms, 218 mmol) and iodoethane (35 g, 218 mmol). The reaction mixture was heated at 40° C. and was followed by TLC. The reaction was complete at the end of 8 hours and quenched with 20% ammonium chloride and extracted with heptane (200 mL). The organic layer was washed with tap water (2×100 mL) and concentrated. Yield: 61 gms (98%).

Example 1b: Synthesis of 2',11-bis(trimethylsilyl)-N-demethyl-4"-deoxy-N-ethylerythromycin B (2a)

N-demethyl-4"-deoxyerythromycin B (50 gms, 72.7 mmol) was dissolved in N-methylprrolidinone (125 mL) and hexamethyldisilazane (38.3 mL, 181.5 mmol) was charged and stirred for 8 hours until the reaction was complete. TLC (80 $CHCl_3$/17MeOH/23 toluene) was performed with p-anisaldehyde stain. Heptane (50 mL) was added to the reaction mixture and then distilled to remove heptane (ammonia gas being liberated). After the distillation was complete, the reaction mixture was cooled and the following reagents were charged: sodium bicarbonate (18.3 g, 218 mmol) and iodoethane (35 g, 218 mmol). The reaction mixture was then heated at 40° C. and followed by TLC (same as above). The reaction was complete at the end of 8 hours. The reaction mixture was extracted with heptane (200 mL) and tap water (100 mL). The organic layer was washed with tap water (2×100 mL) and concentrated. Yield 61.2 gms (98.3%).

Example 1c: Synthesis of 2',11-bis(trimethylsilyl)-N-demethyl-4"-deoxy-N-ethylerythromycin B (2a)

N-demethyl-4"-deoxyerythromycin B (70.5 gms, 102 mmol) was dissolved in N-methylprrolidone (176 mL) and hexamethyldisilazane (53.8 mL, 255 mmol) was charged and stirred for 8 hours until the reaction was complete. TLC (80 $CHCl_3$/17MeOH/23 toluene) was performed with p-anisaldehyde stain. Heptane (70 mL) was added to the reaction mixture and then distilled to remove heptane (ammonia gas being liberated). After the distillation was complete, the reaction mixture was cooled and the following reagents were charged: sodium bicarbonate (18.3 g, 218 mmol) and diethyl sulfate (33.5 mL, 256 mmol). The reaction mixture was then heated at 40° C. and followed by TLC (same as above). The reaction was complete at the end of 8 hours. After the reaction was completed, the reaction mixture was extracted with heptane (250 mL) and tap water (200 mL). The organic layer was washed with tap water (2×100 mL) and concentrated. Yield 61.2 gms (98.3%).

Example 2

Enolization

Example 2a: 8,9-Didehydro-N-demethyl-9-deoxy-4,12"-dideoxy-6,9epoxy-N-ethylerythromycin B (4)

The compound 2',11-bis(trimethylsilyl)-N-demethyl-4"-deoxyerythromycin B (1 Kg, 1.16 mol) from the above Examples was dissolved in DMF (3000 mL) and cooled to 5° C. Dichloroacetic acid (583 mL, 7.06 mmol) was added over a period of 30 minutes and the temperature of the reaction mixture was maintained below 35° C. The reaction was left at room temperature and monitored by TLC (acetone 25/heptane 30/triethylamine 0.2 (v/v)). The reaction was complete after about 10 hours. The reaction mixture was diluted with heptane/ethylacetate (500 mL, 1:1 v/v) and then quenched with triethylamine (977 mL, 7.02 mmol) and 5% sodium bicarbonate solution (300 mL). Layers were separated and the organic layer was washed with distilled water (2×200 mL) and the contents were concentrated to yield the final product. Yield: 780 gms (95%).

Example 2b: 8,9-Didehydro-N-demethyl-9-deoxy-4,12"-dideoxy-6,9epoxy-N-ethylerythromycin B (4)

The compound 2',11-bis(trimethylsilyl)-N-demethyl-4"-deoxyerythromycin B (1 Kg, 1.16 mol) from the above Examples was dissolved in DMF (3000 mL) and cooled to 5° C. Dichloroacetic acid (583 mL, 7.06 mmol) was added over a period of 30 minutes and the temperature of the reaction mixture was maintained below 35° C. The reaction was left at room temperature and monitored by TLC (acetone 25/Heptane 30/triethylamine 0.2 (v/v)). The reaction was complete after about 3 hours. The reaction mixture was diluted with heptane/ethylacetate (500 mL, 1:1 v/v) and then quenched with triethylamine (977 mL, 7.02 mmol) and 5% sodium bicarbonate solution (300 mL). Layers were separated and the organic layer was washed with distilled water (2×200 mL) and the contents were concentrated to yield the final product. Yield: 785 gms (95.6%).

What is claimed is:

1. A process of preparing N-demethyl-N-alkyl-erythromycin derivatives having the formula:

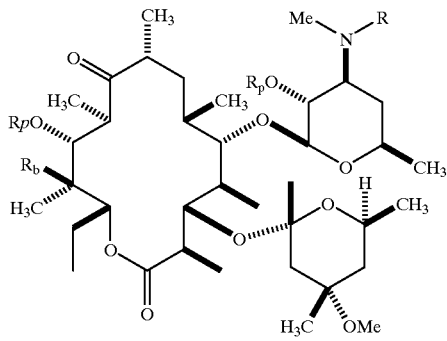

wherein R is a loweralkyl group, $R_b$ is H or OH, and $R_p$ is independently selected at each occurrence from the group consisting of hydrogen and a silyl protecting group, comprising:

a.) protecting a N-demethyl erythromycin A or B compound having the formula:

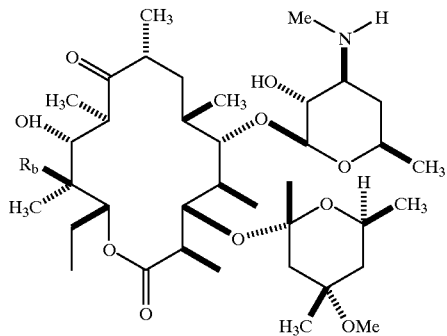

wherein $R_b$ is H or OH, with a silyl protecting group to obtain a compound having a formula:

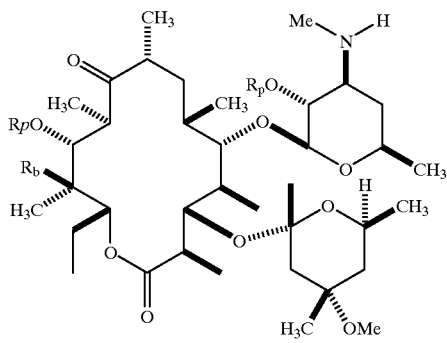

wherein $R_p$ is independently selected at each occurrence from the group consisting of hydrogen and a silyl protecting group and b.) alkylating the the compound obtained in step (a.).

2. A process according to claim 1 wherein the silyl protecting group is selected from a group comprising a silyl group of the formula:

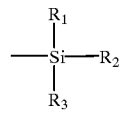

wherein $R_1$, $R_2$, and $R_3$ are each independently selected from the group consisting of triisopropyl, t-butyldimethyl, triethyl, isopropyldimethyl, t-butyldiphenyl, methyldiisopropyl, methyldi-t-butyl, tribenzyl, and triphenyl; $(R_1R_2R_3Si)_nO$ where $R_1$, $R_2$, and $R_3$ are each independently selected from the group consisting of hydrogen and methyl; and $R_3Si$—X, where X is a halide selected from the group consisting of chlorine, bromine, fluorine and iodine, or p-toluenesulfonate or sulfonate.

3. A process according to claim 1 where the silyl protecting reagent is hexamethyldisilazane.

4. A process according to claim 1 wherein the N-demethyl-erythromycin derivative is protected by reacting the N-demethyl erythromycin derivative with a silyl protecting group in the presence of an organic base.

5. A process according to claim 4 wherein the base is selected from a group consisting of N,N-diisopropylethylamine, triethylamine, pyridine, imidazole, ditrimethylsilyl amine, and dimethylaminopyridine.

6. A process according to claim 1 wherein the compound obtained in step (a.) is alkylated by reacting the compound having a formula:

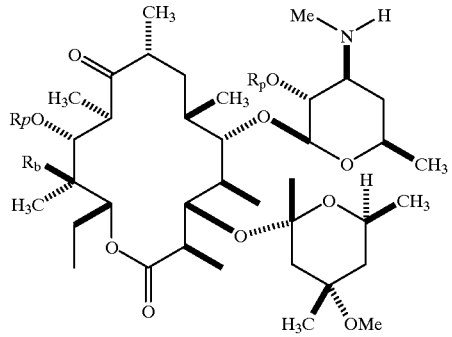

with an alkylating reagent in the presence of a base.

7. A process according to claim 1 wherein the alkylating reagent is selected from a group consisting of R-X, wherein X is selected from the group consisting of bromine, chlorine, fluorine and iodine, sulfate, sulfonate, and p-toluenesulfonate, and R is selected from the group consisting of hydrogen and a lower alkyl group, and diethyl sulfate.

8. A process according to claim 6 wherein the base is selected from a group consisting of sodium bicarbonate, N,N-diisopropylethylamine, triethylamine, sodium dichloracetate, anhydrous sodium acetate, sodium trichloroacetate, and tris(trimethylsilyl)amine.

9. A process according to claim 1 wherein $R_b$ is H.

10. A process according to claim 1 wherein $R_b$ is OH.

11. A process for preparing a compound having a formula:

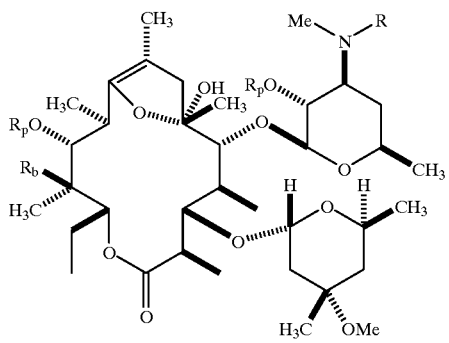

wherein R is a loweralkyl group $R_b$ is H or OH, and $R_p$ is independently selected at each occurrence from the group consisting of hydrogen and a silyl protecting group, comprising reacting a compound having a formula:

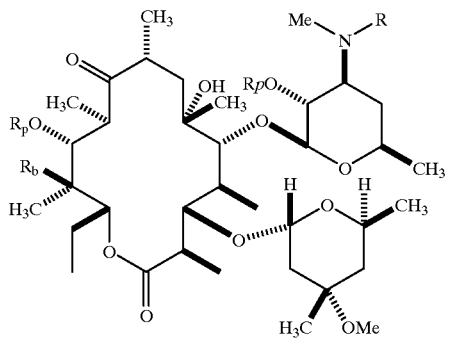

wherein $R_p$ is as defined above, with a weak acid.

12. A process according to claim 11 wherein the weak acid is selected from the group consisting of trifluoroacetic acid, dichloroacetic acid, and acetic acid.

13. A compound having the formula:

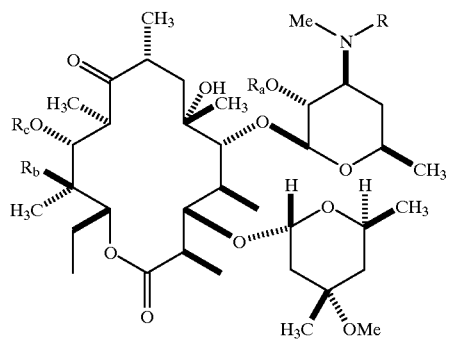

wherein R is a loweralkyl group; $R_b$ is H or OH; and $R_a$ and $R_c$ are each an independently selected silyl protecting group having the formula:

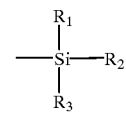

wherein $R_1$, $R_2$, and $R_3$ are each independently selected from the group consisting of triisopropyl, t-butyldimethyl, triethyl, isopropyldimethyl, t-butyldiphenyl, methyldiisopropyl, methyldi-t-butyl, tribenzyl, and triphenyl; $(R_1R_2R_3Si)_nO$ where $R_1$, $R_2$, and $R_3$ are each independently selected from the group consisting of hydrogen and methyl; and $R_3Si$—X, where X is a halide selected from the group consisting of chlorine, bromine, and iodine, or p-toluenesulfonate.

14. A compound according to claim 13 wherein $R_a$ is a silyl protecting group, $R_b$ is OH, and $R_c$ H.

15. A compound according to claim 13 wherein $R_a$ is silyl protecting group, $R_b$ is OH, and $R_c$ is a silyl protecting group.

16. A compound according to claim 13 wherein $R_a$ is silyl protecting group, $R_b$ is H, and $R_c$ is H.

17. A compound according to claim 13 wherein $R_a$ is silyl protecting group, $R_b$ is H, and $R_c$ is silyl protecting group.

* * * * *